United States Patent [19]

Bouma et al.

[11] Patent Number: 5,006,473
[45] Date of Patent: Apr. 9, 1991

[54] ELECTROPHORESIS METHOD USING VESICLES

[75] Inventors: Stanley R. Bouma, Mundelein; Lawrence J. Blecka, Palatine, both of Ill.; Philip Miller, Tucson, Ariz.

[73] Assignee: Abbott Laboratories, Abbott Park, Ill.

[21] Appl. No.: 230,217

[22] Filed: Aug. 9, 1988

[51] Int. Cl.⁵ .......................................... G01N 33/561
[52] U.S. Cl. ........................................ 436/516; 435/4; 435/6; 435/71.1; 435/7.25; 435/7.5; 435/7.9; 435/14; 435/28; 436/512; 436/513; 436/514; 436/515; 436/829; 436/536
[58] Field of Search ................... 436/515, 516, 829; 435/7

[56] References Cited

U.S. PATENT DOCUMENTS

| | | |
|---|---|---|
| 3,966,897 | 6/1976 | Renn et al. |
| 4,599,120 | 12/1985 | Royse et al. |
| 4,605,630 | 8/1986 | Kung et al. |
| 4,628,035 | 12/1986 | Tokinaga et al. |
| 4,704,355 | 11/1987 | Bernstein |
| 4,707,441 | 11/1987 | Ahmad et al. |
| 4,708,933 | 11/1987 | Huang et al. |
| 4,939,098 | 7/1990 | Suzuki et al. ............... 436/514 |

FOREIGN PATENT DOCUMENTS 0162724 11/1985 European Pat. Off.
0244207 4/1987 European Pat. Off.

OTHER PUBLICATIONS

Trampont et al–Chem. Abst. vol. 103 (1985) p. 11479j.

*Primary Examiner*—Sam Rosen
*Attorney, Agent, or Firm*—Daniel R. Curry

[57] ABSTRACT

The electrophoresis method of the present invention employs a media which contains uniformly dispersed liposomes of phospholipid, or combinations of phospholipid and neutral lipid, which contain chromogenic materials or dye precursers. After electrophoresis of a test sample, the liposomes are lysed and the chromogen or dye material released. The chromogen or dye can be any signal producing substance including a chromogenic agent, and enzyme, a fluorogenic agent, or a chemiluminescent agent, but a detectable signal occurs only where the staining material is in close proximity to specific enzymes, effectors, analytes, or other color-inducing agents which have migrated through the gel during electrophoresis.

33 Claims, No Drawings

ELECTROPHORESIS METHOD USING VESICLES

BACKGROUND OF THE INVENTION

The present invention relates to a method and composition for detecting and/or measuring an analyte in a test sample by electrophoresis, and more particularly, to an electrophoresis medium having an indicator reagent in it.

Electrophoresis is widely used to separate the components of a test sample. The technique is based upon the differential movement of charged particles in a supporting medium under the influence of an applied electric field. Bioassay procedures, e.g., antigen-antibody reaction methods, also can be performed by transporting specific binding members (e.g. antibodies and antigens) through the support medium by electrophoresis.

In conventional electrophoresis protocols, after a biological sample has been electrophoresed to form bands from the separated components of the sample, an electropherogram is produced by placing the support medium in a separate bath of developing dye which stains the bands in the medium. Thus, the developing or staining procedure requires a staining chamber or apparatus distinct from the electrophoresis instrument, as well as solutions for staining the medium. Some protocols additionally require a destaining step (and destaining solutions) to remove excess dye from the medium. Thus, the staining procedure requires a sufficient time for the solution to diffuse into and the excess solution to diffuse out of the electrophoresis medium. The laboratory also must provide for storage of the staining and destaining solutions, and for proper disposal of used solutions.

SUMMARY OF THE INVENTION

This invention involves detecting a reactive species in a sample by introducing the sample by electrophoresis into an electrophoresis support media in which liposomes containing an indicator reagent are disposed. Liposomes, due to their size, do not move substantially in the media during electrophoresis. The indicator reagent is reactive with the reactive species to produce a detectable signal which can be detected once the liposomes are lysed to release the indicator reagent, allowing it to react with the reactive species to produce a detectable signal indicative of the presence of the reactive species. Because the media contains liposome-encapsulated indicator reagent, the addition of a developing or staining material and the subsequent removal of excess staining material are unnecessary. Thus, the time required for staining is reduced, and the method is amenable to automated electrophoresis devices. In addition, the method eliminates storage and disposal of staining and destaining solutions.

DETAILED DESCRIPTION OF THE INVENTION

With electrophoresis according to this invention, a reactive species in a sample can be detected if the reactive species is introduced into an electrophoresis media which contains liposomes (or other vesicles) which encapsulate an indicator reagent reactive with the reactive species to produce a detectable signal. Once in the media, the reactive species is detected by lysing the liposomes which releases the indicator reagent, allowing the reactive species and indicator reagent to react, and detecting the detectable signal produced by the reaction.

The "reactive species" can be an analyte in the sample, glucose for example. In a glucose assay, some of the liposomes in the media contain glucose oxidase, others a peroxidase enzyme, and yet others a precipitating substrate for peroxidase. Upon electrophoresis of the glucose-containing sample into the media and lysis of the liposomes, the concentration of glucose can be determined from the intensity of the color generated due to the reaction of glucose oxidase and glucose (which generates hydrogen peroxide), and the activation of the peroxidase by the hydrogen peroxide to produce the color.

Another example where the "reactive species" is an analyte, test samples containing different isoforms of creatine kinase can be subjected to electrophoresis. The support medium can contain liposomes which entrap a precipitating substrate for creatine kinase. After electrophoresis, the liposomes can be lysed, and staining can occur as a result of the reaction between the creatine kinase and the precipitating substrate. The concentration of each isoform of creatine kinase can be determined by measuring the intensity of the signal at each isoform's locus.

In one procedure using a self staining support medium, electrophoresis can be performed on clinical samples containing different isoforms of the enzyme alkaline phosphatase. Electrophoresis separates the isoforms from each other in the support medium, i.e. different isoforms of alkaline phosphatase have different migration patterns in the medium. The support medium can obtain dispersed liposomes which encapsulate a signal producing substance capable of generating a color signal when reacted with alkaline phosphatase. After electrophoresis, the liposomes can be lysed by a pulse of high-voltage electricity. Color formation occurs in the immediate vicinity of the separated isoforms and the newly released signal producing substance. The intensity of the color at the separated bands corresponds with the concentration of isoform at that site. A comparison of the intensities will provide a quantitative comparison of the relative concentrations of each isoform present in the test sample.

The "reactive species" can also be a label attached to an analyte or to an antibody. A "label" is a substance which reacts with the indicator reagent released from the liposomes to produce a detectable signal proportional to the amount of an analyte in the test sample. The selection of a particular label is not critical, but it will be capable of producing a detectable signal in conjunction with the analyte or one or more additional signal producing substances. A variety of different indicator reagents can be formed by varying either the label or the specific binding member. For example, a specific binding member (as defined below) can be attached directly or indirectly to the support medium at a discrete location, i.e., binding zone, within the medium. A labeled analyte, complementary to the specific binding member, will become immobilized in the binding zone during electrophoresis, but non complementary materials will pass through and beyond the binding zone. The analyte itself can be labeled, as in a competitive assay, or the analyte can be labeled through binding with a labeled binding member (e.g. an antibody) specific for the analyte, as in a sandwich assay. Upon lysis of the liposomes, a detectable signal is generated in the binding zone through the reaction of the label and the newly released indicator reagent. The intensity of the signal is proportional to the amount of labeled analyte immobilized within the binding zone. Preferably, the immobilized specific binding member can be bound to or contained in the surface of the liposomes in the support medium, thereby ensuring the proximity of the reactive label and encapsulated indicator reagent. Both forward and reverse assays can be performed.

Multiple analyte assays also can be performed with the present invention. For example, an immunoassay system can be provided wherein several different liposomes are prepared having different surface bound antibodies specific to different analytes in a sample. The liposomes encapsulate an indicator reagent and are immobilized within the support medium to form localized binding zones, i.e., in one distinct zone liposomes having an antibody recognizing hepatitis surface antigen, in a second distinct zone liposomes having an antibody recognizing human immunodeficiency virus, and in a third distinct zone liposomes having an antibody recognizing hepatitis core antigen. The test sample, containing multiple analytes which will bind to the antibodies, is electrophoresed through the medium prior to or simultaneously with a second group of labeled antibodies (i.e., which are labeled with reactive species) which are specific for each of the analytes. The reactive species contain signal precursor, e.g., alkaline phosphatase, that is reactive with the indicator reagents encapsulated within the liposomes. Binding occurs as the analytes and their complementary specific binding members come in contact with one another. Unbound or excess reactive species and unreacted test sample components are removed from the binding zone to another portion of the support medium by electrophoresis. As the liposomes are lysed, either mechanically or by a lysing substance, the presence or amounts of the different analytes in the sample can be detected independently and simultaneously in the three separate zones.

In the case where the analyte is a nucleic acid sequence, a hybridization assay can be performed. A first probe, otherwise known as a capture or separation nucleic acid sequence, is immobilized on the liposomes. A second probe, identified as the indicator or detection nucleic acid sequence, carries a label for the assay. Both probes include different nucleic acid sequences, both complementary to a different portion of the analyte sequence present in the test sample. The sample and detection probe are mixed, sequentially or simultaneously, and subjected to hybridizing conditions and electrophoresis. If the sample contains the analyte sequence, that nucleic acid sequence will provide a bridge between the indicator and capture probes so that a three component hybrid molecule is formed on the liposome by complementary base pairing. Thus, the label becomes associated with the liposome in an amount proportional to the amount of nucleic acid in the sample. The liposomes can be lysed as above so that the analyte can be detected. As a variation of this procedure, rather than immobilizing sample nucleic acids and using a labeled probe, it is also possible to label the sample nucleic acids themselves and thereafter immobilize the labeled sample on the capture probe.

Furthermore, the liposomes or binding zone can be sensitized with an additional specific binding member such as avidin prior to dispersal in the electrophoresis medium. In a hybridization assay, the capture probe can be a modified binding member such as a biotinylated nucleotide. A hybridization reaction can be performed in solution with an analyte sequence and an indicator sequence. The solution can be applied to the support medium, and the reaction product will be immobilized on or near the liposomes through the avidin-biotin binding. Thus, indirect assays using ancillary specific binding members also can be performed.

The signal producing substance or "indicator reagent" can be any material which will directly act with the analyte to make the analyte detectable, or it can be a "stain" precursor which can react with additional agents (e.g. "a label") to generate the detectable signal. The encapsulated signal producing substance is released by lysing the lipid vesicle using techniques described below.

While examples of the present invention mainly discuss the use of chromogenic materials to generate a detectable signal, other signal producing substances can be used. As used herein, a signal producing substance is any substance capable of detection when reacted either with the analyte or with an additional signal precursor(s). Especially useful signal producing substances include enzymes to react with analytes that are enzyme substrates, enzyme substrates to react with analytes that are enzymes, chemiluminescent agents, and fluorogenic agents.

Liposomes are the preferred encapsulating means used in this invention. Liposomes are single or multilayered vesicles obtained when lipids, or particularly lipid mixtures, are dispersed in aqueous suspension. The walls of the vesicles are composed of a continuous lipid layer. Liposomes are the focus of the present invention, but other vesicles can be used, such as cell ghosts, formed by opening a cellular membrane, removing the internal components, and resealing the membrane. The liposomes of the present invention can be made of amphipathic diacyl lipids including sphingomyelin, ceramides, cerebrosides, phosphatidic acid, cardiolipin, or phosphatides of choline, ethanolamine, serine, glycerol, and n-derivatized ethanolamine. These lipids can be used alone, in combination, or mixed with neutral lipids such as cholesterol or tocopherol. For the present invention multilamellar liposomes were constructed.

A number of experiments were undertaken to establish the fate of liposomes during electrophoresis. These experiments were performed to determine whether liposomes migrated in electrophoresis media and whether the liposomes would retain their contents during electrophoresis.

Several electrophoresis protocols were performed in semi-solid agarose gels. In one protocol, liposomes containing a dye material were mixed with an equal volume of hot agarose. After the agarose hardened, the gel was immersed in buffer. Electrophoresis was started and maintained for at least an hour, but the liposome-encapsulated dye did not migrate in the field. The liposomes were then lysed, and electrophoresis was resumed for thirty minutes. Dye which has been released from the liposomes migrated in the electric field and was washed away from the liposomes.

In another protocol, liposomes containing a dye material were mixed with a free dye and hot agarose. After the agarose hardened, the gel was immersed in buffer and electrophoresis performed for at least an hour. The free dye migrated during electrophoresis, but the liposome-encapsulated dye did not. The liposomes were lysed, and electrophoresis resumed for about thirty minutes, forcing the newly released dye material to migrate.

The experiments demonstrated several points. First, liposomes (except for very small vesicles) do not migrate in support media during electrophoresis. Second, liposomes can retain their contents during electrophoresis. Third, liposomes can be made to release their contents in the support media. And fourth, electrophoresis can wash liposomes very clean of unencapsulated material.

It was discovered that liposomes larger than 50 nm in diameter do not migrate during electrophoresis, and are thus suitable for use in self-staining media. Liposomes having a diameter greater than one $\mu$m are preferred, however, because the volume of entrapped signal producing substance is larger. A liposome with a one $\mu$m diameter will encapsulate one thousand times the amount of signal producing substance as a liposome having a diameter of 100 nm. No liposomes of any size have been found to impede the migration of other macromolecules through the support medium during electrophoresis.

Lysis of the liposomes within the support media can be achieved by a variety of methods. These methods include exposure of the liposomes to a detergent, a freeze thaw cycle, sonication, high voltage electricity, or light (photolysis). Immunolysis can also be used, e.g., when a liposome membrane contains an externally accessible antigen, that antigen can react with a corresponding antibody lysing, in the presence of complement, the liposomal membrane and releasing the signal producing substance.

The "support medium" can be any matrix-forming material in or to which the liposomes can be fixed and through which test sample can diffuse or pass. For electrophoresis, the preferred support medium is a semi-solid matrix-forming material such as agarose or a chemically modified agarose. Other semi-solid matrix-forming materials include, but are not limited to, acrylamide, starch, cellulose, and derivatives thereof.

A "specific binding member", as used herein, is a member of a specific binding pair, i.e., two different molecules where one of the molecules through chemical or physical means specifically binds to the second molecule. Therefore, in addition to antigen and antibody or hapten and antibody specific binding pairs, other specific binding pairs can include, as examples without limitation, biotin and avidin, carbohydrates and lectins, complementary nucleotide sequences, effector and receptor molecules, enzyme cofactors and enzymes, enzyme inhibitors and enzymes, and the like. Furthermore, specific binding pairs can include members that are analogs of the original specific binding member, for example an analyte-analog. If the specific binding member is an immunoreactant it can be, for example, an antibody, antigen, hapten, or complex thereof, specific for the analyte of interest, and if an antibody is used, it can be a monoclonal or polyclonal antibody, a recombinant antibody, a mixture(s) or fragment(s) thereof, as well as a mixture of an antibody and other specific binding members, as well as specific binding members formed by recombinant DNA methods. The details of the preparation of such antibodies and their suitability for use as specific binding members are well known and will not be repeated here.

"Analyte", as used herein, is the substance to be detected or separated from the sample using the present invention. The analyte can be any substance for which there exists a naturally occurring specific binding member (e.g., an antibody) or for which a specific binding member can be prepared. Thus, an analyte is a substance that can bind to one or more specific binding members in an assay. "Analyte" also includes any antigenic substances, haptens, antibodies, and combinations thereof. As a member of a specific binding pair, the analyte can be detected by means of a naturally occurring specific binding partner, such as the use of intrinsic factor protein in the capture and/or indicator reagents for the determination of vitamin $B_{12}$, or the use of a lectin in the capture and/or indicator reagents for the determination of a carbohydrate. The analyte can include, but is not limited to, a protein, a peptide, an amino acid, a hormone, a steroid, a nucleic acid, a vitamin, a drug including those administered for therapeutic purposes as well as those administered for illicit purposes, a bacterium, a virus, and metabolites of or antibodies to any of the above substances.

Sample fluids on which tests can be performed include biological, physiological, industrial, environmental, and other types of liquids. Of particular interest are the biological fluids such as serum, plasma, urine, cerebrospinal fluid, saliva, milk, broth and other culture media and supernatants as well as fractions of any of them.

The specific separation of sample components by electrophoresis, in combination with a signal production that is limited to the vicinity of the analyte, provides a highly visible separation with very low background. The process enables the separation of sample components in 15 to 20 minutes and the development of the medium within 5 to 10 minutes. Because there is no need for separate staining solutions and procedures, the invention lends itself to use in an automated electrophoresis protocol, as well as to adaptation for multiple assays from a single aliquot of sample.

EXAMPLES

The following examples illustrate preferred ways of making the novel materials of the present invention and performing assay procedures using those materials. The examples, however, are intended only to be illustrative, and are not to be construed as placing limitations upon the scope of the invention.

EXAMPLE 1

Preparation of liposomes

Egg sphingomyelin (~95% palmitoyl. 13.5 umole), cholesterol (15 umole) and dipalmitoylphosphatidylglycerol (1.5 umole) were dissolved into a single solution in a solvent of 90% chloroform and 10% methanol. The solvent was removed by rotary evaporation, and the lipids were redissolved in 90% chloroform and 10% methanol. The solvent was removed again, by rotary evaporation and evacuation under high vacuum.

The lipid film thus formed was placed in a flask and was hydrated with an aqueous solution containing the staining material 5-bromo-4-chloro-3-indolyl phosphate (100 mM BCIP; 10 mM glycine, 10 uM $ZnCl_2$ and sufficient TRIS-hydroxyethylaminomethane [TRIS] to obtain a pH of 8.0). Hydration was accomplished by allowing the flask to rotate slowly for three hours, in the dark, so that the entire lipid film came into repeated contact with the solution. Any remaining lipid film was suspended in the solution by forcing the mixture into and out of a pasteur pipette. To form the liposomes, the lipid suspension was extruded five times through a polycarbonate filter having uniform 10 um pores (Nucleopore Corporation, Pleasanton, Calif.). The liposomes were washed by diluting them in a buffer (10 mM glycine, 100 uM $ZnCl_2$, and sufficient TRIS to achieve pH 8.0) and centrifuging them for six minutes at about $3,000 \times g$. The wash procedure was then repeated.

EXAMPLE 2

Preparation of self-staining electrophoresis media

DNA-grade agarose (260 mg) was dissolved in a buffer (e.g., 26 mL of 100 mM glycine, 100 uM $ZnCl_2$, and sufficient TRIS to achieve pH 8.0, or 100 mM TRIS and boric acid to make pH 8.5) with gentle boiling for five minutes. The solution was cooled to about 55° C., at which time approximately 300 uL of the liposomes of Example 1 were added. The mixture was then poured into a casting chamber and cooled to make a flat gel (10 cm long $\times$ 6.5 cm wide $\times$ about 0.35 cm thick). The casting chamber contained a comb to form agarose-free wells in the gel such that sample could be introduced to the gel through the wells at a later time.

EXAMPLE 3

Electrophoresis protocol

Electrophoresis was performed by standard methods. The hardened agarose gel was placed in an apparatus designed for submarine electrophoresis (Bio-Rad, Richmond Calif.) and submerged under one to two millimeters of buffer of the same composition as that used to form the gel. Samples were applied to the wells created by combs or into areas carved out of the gel. A voltage of 50 V to 300 V was applied to the gel for 0.25 to 4 hours to cause the lateral migration of the various analytes and test reagents through the support medium.

EXAMPLE 4

In situ lysis of liposomes in an electrophoresis gel

The lysis of liposomes in the gel was performed by a variety of methods. Lysis by detergent was achieved by placing a solution of detergent (10 uL of 24% octyl-D-glucopyranoside) onto the electrophoresis gel directly over the liposomes. The detergent reached the liposomes by simple diffusion into the gel.

Lysis by a freeze thaw cycle was achieved by placing the gel into a freezer at −70° C. for at least 15 minutes and then allowing the gel to warm to room temperature.

Lysis by ultrasonication was achieved by one of two methods. In the first method, the gel was placed in plastic wrap, and the wrap was lowered into an ultrasonic cleaning bath containing about two millimeters of water. The gel was irradiated with ultrasound for about seven minutes. In the second method, an ultrasonic probe was lowered onto the gel so that the probe's tip made contact with the gel directly above the liposomes. This locus was irradiated with ultrasound for periods ranging from two seconds to more than one minute.

Lysis by high-voltage shock was achieved by placing the gel between two acrylic plates to which were attached electrodes of copper, steel, or brass. The gel was positioned such that the liposomes were directly between the electrodes, and the gel made contact with each electrode. The electrodes were connected to a circuit capable of delivering pulses of electricity of up to 15,000 V and about one usec in duration. A number of pulses (from one to more than 20) were delivered throught the liposome-containing gels.

In most cases, lysis was demonstrated by subjecting the support medium to further electrophoresis so that the newly released signal producing substance would migrate away from the locus of the liposomes. In other cases, lysis was demonstrated by reacting the newly released signal producing substance with other reagents which were electrophoresed through the support medium. For example, newly released BCIP was reacted with extra-liposomal alkaline phosphatase to yield a blue-colored product. Only BCIP that was released in the vicinity of alkaline phosphatase yielded a colored product in the support medium.

EXAMPLE 5

Electrophoresis of alkaline phosphatase-antibody conjugate

Multilamellar liposomes were prepared of spingomylin, cholesterol, and phosphatidylglycerol as in Example 1. The liposomes contained BCIP as a signal producing substance or substrate for alkaline phosphatase. The liposomes were mixed at 45° C. with a solution of one percent agarose, and the mixture was cast into a mold and cooled to form a semi-solid electrophoresis gel.

Samples of alkaline phosphatase-conjugated antibody were placed in wells within the gel. The samples were made to migrate laterally into the gel by the force of an applied electric field (300 V for 15 minutes).

After electrophoresis, the gel was placed in a freezer (−70° C. for 15 minutes) and then thawed at room temperature. The lysed liposomes released the encapsulated BCIP more or less uniformly throughout the gel. The reaction of the BCIP and alkaline phosphatase formed a colored precipitate only in the vicinity of the alkaline phosphatase antibody conjugate, leaving the majority of the gel free from developed color.

EXAMPLE 6

Binding of DNA to liposomes

The liposomes used were multilamellar vesicles made of spingomyelin, cholesterol, and phosphatidyl-3-thioglycerol (PTG) in a ratio of 45:50:5, to which had been bound avidin via a covalent linkage to the PTG. The liposomes encapsulated calcein (100 mM), a fluorogenic agent.

Two procedures were employed to detect the specific binding of biotinylated DNA to the avidin-liposomes. In the first procedure, liposomes, biotinylated DNA, and non biotinylated DNA (control DNA) were preincubated for one hour at room temperature and were then added to the sample well. After electrophoresis, the DNA bound to the liposomes by the avidin/biotin specific binding pair remained at the origin whereas the unbound non biotinylated DNA migrated into the gel. In the second procedure, avidin-liposomes were precast in a section of an agarose gel away from the sample wells. When the gel hardened, biotinylated DNA and control DNA were added to the sample wells. With electrophoresis, the biotinylated DNA bound to the avidin-liposomes as it passed through the liposome section of the gel, but the control DNA migrated through the medium without binding.

The result was virtually quantitative binding of DNA to liposomes. The experiment also demonstrated the rapid binding of DNA to liposomes, the rate of which can be estimated from the migration rate of DNA (about 2.5 cm/hour) and the size of the liposomes (about one um). The rate of 2.5 cm/hour is about seven um/sec, so the average DNA molecule has about 145 msec to encounter the average liposome. Rapid binding of DNA can be made more quantitative by employing more liposomes.

The concepts of the present invention are applicable to various types of assays. It will be appreciated that one skilled in the art can conceive of many other signal producing assays to which the present inventive concepts can be applied. The embodiments described and the alternative embodiments presented are intended as examples rather than as limitations. Thus, the description of the invention is not intended to limit the invention to the particular embodiments disclosed, but it is intended to encompass all equivalents and subject matter within the spirit and scope of the invention as described above and as set forth in the following claims.

We claim:

1. A method for detecting an analyte of interest in a sample comprising:
   (a) providing an electrophoresis support medium through which said sample can migrate, said support medium including
      (i) vesicles in which an indicator reagent is encapsulated, wherein said vesicles are embedded in said support medium and are of sufficient size so as to be immobile in said support medium, and
      (ii) first binding members immobilized in said support medium, wherein said first binding members are capable of binding said analyte, and wherein said first binding members are immobilized directly within said support medium or indirectly by immobilization upon said vesicles;
   (b) passing said sample through said support medium by electrophoresis so analyte is bound by said first binding members;
   (c) passing a reactive species through said support medium, wherein said reactive species is a label, and wherein said label is capable of reacting with said indicator reagent in the presence of analyte to produce a detectable signal;
   (d) lysing said vesicles; and
   (e) detecting said signal.

2. The method according to claim 1 wherein said vesicles are lysed by photolysis, detergent, sonication, freeze-thaw cycling, immunolysis, or electricity.

3. The method of claim 1 wherein said reactive species is bound to second binding members capable of binding to said analyte.

4. The method of claim 3 wherein plural pairs of first and second binding members are employed, each pair being specific to a different analyte, whereby plural analytes can be detected.

5. The method of claim 4 wherein each of first binding members for one analyte is disposed in a zone in said media distinct from the first binding members for other analytes.

6. The member according to claim 1 wherein said indicator reagent is selected from an enzyme, enzyme substrate, chromogen, chemiluminescent agent, and a fluorogenic agent.

7. The method according to claim 3 wherein said analyte is DNA, and said first and second binding members are oligonucleotide sequences capable of hybridizing simultaneously with said DNA.

8. The method of claim 3 wherein said analyte is an antigen, and said first and second binding members are antibodies capable of binding simultaneously with said antigen.

9. The method according to claim 1, further comprising the step of continuing electrophoresis after lysing said vesicles, thereby separating reacted indicator reagent from unreacted indicator reagent to facilitate the detection of said signal.

10. The method according to claim 1, wherein there are a plurality of said vesicles and different vesicles contain different indicator reagents.

11. A method for detecting or quantitating an analyte of interest in a test sample, comprising:
   (a) contacting the test sample to an electrophoresis support medium through which the test sample can migrate, said medium including a signal-producing substance capable of reacting with the analyte, said signal-producing substance being encapsulated in vesicles positioned in said matrix-forming material, wherein said vesicles are embedded in said support medium and are of sufficient size so as to be immobile in said support medium;
   (b) transporting the test sample through said support medium by electrophoresis;
   (c) lysing said vesicles; and
   (d) detecting or quantitating said detectable signal.

12. The method according to claim 11, wherein said vesicles are lysed by photolysis, detergent, sonication, freeze-thaw cycle, immunolysis, or electricity to said support medium.

13. The method according to claim 11, wherein said signal producing substance is an enzyme, an enzyme substrate, a chromogenic agent, a chemiluminescent agent, or fluorogenic agent.

14. The method according to claim 11, further comprising the step of continuing electrophoresis after lysing said vesicles, thereby separating reacted signal producing substance from unreacted signal producing substance to facilitate the detection of said signal.

15. The method according to claim 11, wherein said vesicles are liposomes.

16. The support medium according to claim 11, wherein there are a plurality of said vesicles and different vesicles contain different signal producing substances.

17. A method for detecting or quantitating an analyte of interest in a test sample, comprising:
   a. simultaneously or sequentially combining
      (i) the test sample,
      (ii) a labeled first specific binding member, and
      (iii) a second specific binding member immobilized directly within an electrophoresis support medium or indirectly by immobilization upon vesicles with said support medium, said support medium comprising a matrix-forming material through which the test sample can migrate during electrophoresis, and a signal producing substance capable of reacting with said label to produce a detectable signal, wherein said signal producing substance is encapsulated in said vesicles, and wherein said vesicles are embedded in said support medium and are of sufficient size so as to be immobile in said support medium;
   b. immobilizing said labeled first specific binding member in said support medium by direct or indirect association with said second specific binding member;
   c. lysing said vesicles; and
   d. detecting or quantitating the detectable signal.

18. The method according to claim 17, wherein said first specific binding member and said second specific binding member are specific for the analyte.

19. The method according to claim 17, wherein said second specific binding member is specific for said first specific binding member and the analyte.

20. The method according to claim 17, wherein said labeled first specific binding member is transported through said support medium by electrophoresis simultaneously with the test sample.

21. The method according to claim 17, wherein said second specific binding member is immobilized in at least one discrete zone in said support medium.

22. The method according to claim 21, wherein said vesicles are located in said binding zone.

23. The method according to claim 22, wherein said second specific binding member is attached to said vesicles.

24. The method according to claim 17, further comprising the step of continuing electrophoresis after lysing said vesicles, thereby separating reacted signal producing substance from unreacted signal producing substance to facilitate the detection of said signal.

25. The method according to claim 17, wherein said vesicles are liposomes.

26. The support medium according to claim 17, wherein there are a plurality of said vesicles and different vesicles contain different signal producing substances.

27. A method for detecting or quantitating an analyte of interest in a test sample, comprising:
 a. simultaneously or sequentially combining
   (i) the test sample,
   (ii) a labeled first binding member specific for the analyte,
   (iii) a second binding member specific for the analyte, and
   (iv) a third binding member, specific for said second binding member, immobilized directly within an electrophoresis support medium or indirectly by immobilization upon vesicles with said support medium, said support medium comprising, a matrix-forming material through which the test sample can migrate during electrophoresis, and a signal producing substance capable of reacting with said label to produce a detectable signal, wherein said signal producing substance is encapsulated in said vesicles, and wherein said vesicles are embedded in said support medium and are of sufficient size so as to be immobile in said support medium;
   whereby the analyte, said labeled first binding member and said second binding member form a complex immobilized in said support medium by binding to said third specific binding member;
 b. lysing said vesicles; and
 c. detecting or quantitating the detectable signal.

28. The method according to claim 17, wherein said first, second and third specific binding members are selected from the group of specific pairs consisting of biotin and avidin, carbohydrates and lectins, complementary nucleotide sequences, effector and receptor molecules, enzyme cofactors and enzymes, enzyme inhibitors and enzymes, and immunoreactants.

29. The method according to claim 28, wherein said immunoreactants are selected from the group consisting of a monoclonal antibody, polyclonal antibody, antibody fragment, recombinant antibody, antigen, and complexes thereof.

30. The method according to claim 27, wherein the analyte is DNA, and said first and second binding members are oligonucleotide sequences capable of hybridizing with the analyte.

31. The method according to claim 30, wherein said second binding member is a complex of biotin and a nucleotide sequence complementary to the analyte.

32. The method according to claim 31, wherein said third binding member is specific for biotin.

33. The method according to claim 27, wherein said second binding member is a complex of at least two different binding members, and wherein one binding member binds to the analyte and one binding member binds to said third binding member.

* * * * *